United States Patent [19]

Beard et al.

[11] Patent Number: 4,925,962

[45] Date of Patent: May 15, 1990

[54] TRIMETHYLALUMINUM PROCESS

[75] Inventors: William R. Beard; Herbert M. Scull, both of Baton Rouge, La.

[73] Assignee: Ethyl Corporation, Richmond, Va.

[21] Appl. No.: 261,610

[22] Filed: Oct. 24, 1988

[51] Int. Cl.$^5$ ............................................. C07F 5/06
[52] U.S. Cl. ................................................... 556/187
[58] Field of Search ......................................... 556/187

[56] References Cited

U.S. PATENT DOCUMENTS

| | | | |
|---|---|---|---|
| 3,288,828 | 11/1966 | Wartik et al. | 556/187 |
| 4,364,872 | 12/1982 | Diefenbach | 556/187 |
| 4,364,873 | 12/1982 | Diefenbach . | |
| 4,364,874 | 12/1982 | Diefenbach . | |

OTHER PUBLICATIONS

Batalov et al., "Doklady Akademii Nauk. SSR", vol. 136, No. 1, pp. 93–95.
Korshunov et al., "Zhurnal Obshchei Khimii", vol. 31, No. 3, pp. 964–969.

*Primary Examiner*—Werren B. Lone
*Attorney, Agent, or Firm*—Joseph D. Odenweller

[57] ABSTRACT

Trimethylaluminum is made by gradually feeding a methyl halide to a reaction vessel containing a tri-$C_{2+}$ alkylaluminum (e.g. triethylaluminum) and a catalyst formed from a bismuth compound and an alkyl or aryl organoaluminum compound thereby forming trimethylaluminum and $C_{2+}$ alkyl halide and continuously distilling the $C_{2+}$ alkyl halide, and any methyl halide that fails to react, from the reaction vessel thereby avoiding the accumulation of trialkylaluminum and alkyl halide which not only tends to form alkylaluminum halides but can be very hazardous on a large scale if a temperature excursion should occur.

20 Claims, No Drawings

TRIMETHYLALUMINUM PROCESS

BACKGROUND

Unlike the ethyl and higher trialkylaluminum compounds which can be made economically by reactions of aluminum, hydrogen, and an olefin, trimethylaluminum has been produced only by processes which begin with a methyl halide. These include the direct reaction of a methyl halide with aluminum metal to form the methylaluminum sesquihalide, followed by a reduction step generally utilizing sodium as the reducing agent. Thus, starting with methyl chloride as a source of the methyl group:

$$3CH_3Cl + 2Al \rightarrow (CH_3)_3Al_2Cl_3$$
$$(CH_3)_3Al_2Cl_3 + 3Na \rightarrow (CH_3)_3Al + 3NaCl + Al$$

This process has been used on a commercial scale to produce trimethylaluminum. Processes of this type are described in an article by A. V. Grosse and J. M. Mavity, *Journal of Organic Chemistry*, 5, 106 (1940), and in U.S. Pat. Nos. 2,863,894 and 2,954,389.

U.S. Pat. No. 2,744,127 describes a related method involving the direct reaction of a 40Al/60Mg alloy with a methyl halide, according to the equation:

$$CH_3Cl + Al_2Mg_3 \rightarrow 2(CH_3)_3Al + 3MgCl_2$$

A method described in U.S. Pat. No. 2,839,556 does not use a reducing metal but is based on formation of cryolite as a means of removing halogen from a methylaluminum halide. For example, $$(CH_3)_2AlCl + NaF \rightarrow (CH_3)_2AlF + NaCl$$
$$3(CH_3)_2AlF + 3NaF \rightarrow 2(CH_3)_3Al + Na_3Al_2F_6$$

All of the above-described methods have the disadvantage of forming very large amounts of inorganic metal halide by-products. These materials not only have very low value, but are also generally produced in forms which makes their recovery uneconomical. Hence they must be disposed of in a safe and ecologically acceptable manner, which adds further economic penalty to the trimethylaluminum synthesis.

Reviews of organoaluminum compound synthesis, e.g., in "Organoaluminum Compounds" by T. Mole and E. A. Jeffery (Elsevier, N.Y., 1972) describe other methods of trimethylaluminum synthesis generally not useful for economic commercial production. These include the initial preparation of a Grignard reagent, CH$_3$MgX, and its reaction with an aluminum halide in an ether solvent, $$3CH_3MgX + AlX_3 \rightarrow (CH_3)_3Al + 3MgX_2$$

which cannot be removed readily from the trimethylaluminum product. Another route, which has been of academic interest only, is initial synthesis of very toxic dimethylmercury (from a CH$_3$MgX reagent), from which the mercury can be displaced by aluminum in a solvent-free reaction.

$$3(CH_3)_2Hg + 2Al \rightarrow 2(CH_3)_3Al + 3Hg$$

A recent patent, U.S. Pat No. 4,118,409, provides for jointly making trimethylaluminum and alkylaluminum bromides and iodides in an alkyl exchange process by mixing an aluminum trialkyl, such as triethylaluminum, and a methylaluminum bromide or iodide and then distilling from the mixture trimethylaluminum as a first fraction and then alkylaluminum bromides or iodides as a subsequent fraction.

Still more recently S. P. Diefenbach has described several methods for making trimethylaluminum from triethylaluminum. In U.S. Pat No. 4,364,872, triethylaluminum is reacted with a methyl halide in the presence of a catalyst formed from a bismuth compound, e.g. BiCl$_3$. The reaction is conducted in an autoclave.

Diefenbach U.S. Pat No. 4,364,873 describes a similar process using a catalyst formed from a vanadium compound (e.g. VOCl$_3$), a trialkylaluminum (e.g. triethylaluminum) and an alkyl iodide.

Diefenbach U.S. Pat. No. 4,364,474 describes a trimethylaluminum process using a non-catalyzed alkyl exchange between a higher trialkylaluminum such as triethylaluminum and methyl iodide.

Of the foregoing alkyl exchange systems, the most cost-effective process appears to be that shown in U.S. Pat. No. 4,364,872. Although the process of U.S. Pat. No. '872 is very effective on a laboratory scale, certain problems are encountered in conducting the process on a commercial scale. In U.S. Pat. No. '872, all of the tri-C$_{2+}$ alkylaluminum and methyl halide is present together with the bismuth catalyst at the start of the reaction in a sealed autoclave. As the reaction proceeds, methyl halide is consumed and C$_{2+}$ alkyl halide forms so the ratio of alkyl halide to trialkylaluminum is always high during the process. Alkyl halide can react with trialkylaluminum to form various alkylaluminum halides which consumes either trimethylaluminum product or the higher trialkylaluminum used as a reactant forming alkylaluminum halide.

Of greater concern in reaction mixtures containing high ratios of alkyl halide to alkylaluminum compound, is the possibility of a thermal excursion in a large scale reactor which can lead to an explosive reaction between the alkylaluminum compounds and the alkyl halides.

SUMMARY

According to the present invention, an improvement is provided in the process of U.S. Pat No. 4,364,872 whereby methyl halide is fed to the reaction zone at a controlled rate while concurrently distilling C$_{2+}$ alkyl halide from the reaction zone thereby avoiding the presence of large amounts of both aluminum trialkyls and alkyl halides in the reaction zone at the same time.

DESCRIPTION OF THE PREFERRED EMBODIMENTS

A preferred embodiment of the process resides in an improvement in a process for making trimethylaluminum by reacting a methyl halide with a trialkylaluminum which has at least two carbon atoms in its alkyl groups in the presence of a catalyst formed from a bismuth compound and recovering trimethylaluminum from the resultant reaction mixture. According to the improvement, methyl halide is added to a reaction mixture containing a tri-C$_{2+}$ aluminum alkyl and said catalyst formed from said bismuth compound at a controlled rate such that said methyl halide reacts as it is added to form trimethylaluminum and C$_{2+}$ alkyl halide while continuously distilling said C$_{2+}$ alkyl halide and any unreacted methyl halide from the reaction zone thereby avoiding accumulation of either methyl halide or C$_{2+}$ alkyl halide in the reaction mixture.

The basic process is described in detail in Diefenbach U.S. Pat. No. 4,364,872 which is incorporated herein in its entirety as if fully set forth.

Trialkylaluminum compounds in which the alkyl groups contain at least two carbon atoms include triethylaluminum, tri-n-propylaluminum, tri-n-butylaluminum, tri-isobutylaluminum, tri-n-pentylaluminum, trihexylaluminum, trioctylaluminum. By far the most preferred tri-$C_{2+}$ alkyl aluminum compound is triethylaluminum because it is readily available at reasonable cost.

Useful methyl halides include methyl chloride, methyl bromide and methyl iodide.

Any bismuth compound can be used to prepare the catalyst. It is believed that the bismuth compound reacts with the trialkylaluminum to form a compound which contains bismuth, aluminum and alkyl groups and possibly other groups. It is not necessary to know the structure of the active catalyst specie in order to obtain the benefits of the reaction.

Preferred bismuth compounds are bismuth halides and organobismuth compounds. Examples are bismuth trichloride, bismuth triiodide, bismuth tribromide, bismuth trifluoride, triphenylbismuth, pentaphenylbismuth, trimethylbismuth, diphenylbismuth chloride, triethylbismuth, triphenylbismuth dichloride, bismuth triethoxide, bismuth triacetate, diethylbismuth bromide and the like.

Any trialkylaluminum can be used to form the catalyst including trimethylaluminum. In a most preferred embodiment bismuth trichloride is reacted with triethylaluminum to form the catalyst.

The amount of bismuth compound used in the process can vary over a wide range. A useful range is about 1–25 mole percent based on the total amount of tri-$C_{2+}$ alkyl aluminum used in the reaction. A preferred range is about 2–10 mole percent and most preferably about 3–7 mole percent.

The process can be conducted in a solvent although this is not essential. Useful solvents include the inert liquid aliphatic hydrocarbons such as hexane, octane, decane, cyclohexane, cyclooctane. Aromatics such as benzene, toluene, xylene and the like can be used although this may lead to some nuclear alkylation.

Useful reaction temperatures are those that cause the exchange reaction to proceed at a reasonable rate but not so high as to cause the reactants or products to undergo undesired decomposition. A useful temperature range is about 50°–75° C. A more preferred temperature range is about 90°–125° C. Temperatures above 127° C. will require some pressure in the reactor so the trimethylaluminum does not vaporize.

In one mode of operation, the process can be carried out by placing all of the tri-$C_{2+}$ alkyl aluminum reactant and the bismuth compound in a reaction vessel under an inert atmosphere such as nitrogen which is stirred and heated to reaction temperature. Then the methyl halide is introduced into the liquid phase at a controlled rate such that an excessive amount of methyl halide does not collect in the reactor. Most of the methyl halide will react with the tri-$C_{2+}$ alkyl aluminum under these conditions to form $C_{2+}$ alkyl halide. The reaction temperature must be high enough such that this $C_{2+}$ alkyl halide will vaporize from the reaction mixture. For example ethyl chloride has a normal boiling point of 12.3° C., ethyl bromide 38.4° C. and n-butyl chloride 78.5° C.

The reaction is conducted at atmospheric pressure or close to atmospheric pressure so the lower $C_{2+}$ alkyl halide will readily vaporize. Part of the methyl halide will also escape the liquid reaction phase and be conducted from the reaction vessel together with the $C_{2+}$ alkyl halide. In practice about 4–5 moles of methyl halide will be injected into the liquid reaction phase per mole of tri-$C_{2+}$ alkyl aluminum to be converted to trimethylaluminum. The vented methyl halide and $C_{2+}$ alkyl halide can be condensed and separated by conventional means.

Progress of the reaction can be monitored by periodically withdrawing small samples and analyzing them. When the reaction is complete, trimethylaluminum can be recovered from the reaction mixture by fractionation. Trimethylaluminum has a normal boiling point of 127° C. so the distillation can be conducted at atmospheric pressure. If desired, the fractionation can be conducted at reduced pressure if the system is leakproof.

Another mode of operation comprises:

(A) forming a catalyst mixture in a reaction zone by reacting a trialkylaluminum with a bismuth compound, (B) continuously feeding to said reaction zone (i) trialkylaluminum wherein the alkyl groups contain at least two carbon atoms and (ii) at least a stoichiometric amount, based on the formation of trimethylaluminum, of a methyl halide whereby said trialkylaluminum feed and said methyl halide react to form trimethylaluminum and a $C_{2+}$ alkyl halide, (C) continuously distilling said $C_{2+}$ alkyl halide and any unreacted methyl halide from said reaction zone and (D) recovering trimethylaluminum from said reaction zone.

In this embodiment the reactants and catalysts are the same as in the previous embodiment. It differs in that both the methyl halide and tri-$C_{2+}$ alkyl aluminum are continuously fed to the reaction zone which contains the catalyst. The catalyst is preferably formed in the reaction zone by combining a trialkylaluminum and a bismuth compound in an aliphatic hydrocarbon solvent having at boiling point above the reaction temperature. Normal decane (b.p. 174° C.) is a preferred solvent. The mixture is stirred and heated to reaction temperature and then both tri-$C_{2+}$ alkyl aluminum, e.g. triethylaluminum, and methyl halide are concurrently fed to the reaction zone at a controlled rate. The methyl halide is preferably injected into the liquid phase. A preferred mole ratio of methyl halide to tri-$C_{2+}$ alkyl aluminum is about 3–6:1 and more preferably about 4–5:1.

The methyl halide will enter into an alkyl exchange reaction with the tri-$C_{2+}$ alkyl aluminum forming trimethylaluminum and $C_{2+}$ alkyl halide. The $C_{2+}$ alkyl halide will vaporize at the reaction temperature and be conducted out of the reaction zone. As before, a portion of the methyl halide will escape the liquid phase and pass out of the reactor together with the $C_{2+}$ alkyl halide. This is why a stoichiometric excess of methyl halide is used.

After the addition of the tri-$C_{2+}$ alkyl aluminum and methyl halide is complete, the mixture is stirred at reaction temperature and then analyzed to be sure most of the tri-$C_{2+}$ alkyl aluminum has been converted to trimethylaluminum. Trimethylaluminum can then be recovered from the reaction mixture by fractionation.

The process can also be conducted in a continuous manner comprising:

(A) forming a catalyst mixture in a reaction zone by reacting a trialkylaluminum with a bismuth compound, (B) continuously feeding to said reaction zone (i) trialkylaluminum wherein the alkyl groups contain at least two carbon atoms and (ii) at least a stoichiometric amount, based on the formation of trimethylaluminum, of a methyl halide whereby said trialkylaluminum feed and said methyl halide react to form trimethylaluminum and a $C_{2+}$ alkyl halide, (C) continuously distilling said trimethylaluminum, said $C_{2+}$ alkyl halide and any unreacted methyl halide from said reaction zone and, (D) recovering trimethylaluminum from the distillate.

This embodiment of the process uses the same reactants and catalyst as the previous embodiment. It also uses the same concurrent addition of both methyl halide and tri-$C_{2+}$ alkyl aluminum to the reaction zone using a stoichiometric excess of methyl halide. It differs in that the reaction temperature and pressure are such that the trimethylaluminum formed in the reaction distills out together with the $C_{2+}$ alkyl halide and any unreacted methyl halide. Since trimethylaluminum has a normal boiling point of about 127° C. it is preferred to conduct this embodiment above 127° C., for example 130°–175° C., more preferably 135°–150° C. Optionally the process can be conducted at reduced pressure to lower the boiling point of trimethylaluminum. Reduced pressure operation is not preferred because of the hazards of any air leak into the reaction system which could lead to a violent reaction.

The continuous process can also be conducted with an inert solvent in the reaction zone which boils higher than trimethylaluminum. Aliphatic hydrocarbons such as n-decane are preferred.

The vapor removed is preferably condensed in two stages. The first condenser is operated at a temperature such that the trimethylaluminum condenses but not the alkyl halides. The alkyl halides are then condensed downstream in a second condenser operated at a lower temperature.

The following examples serve to show how the process is carried out.

EXAMPLE 1

A 250-ml three-necked round bottomed reaction flask which was equipped with a one-inch Teflon coated magnetic stirring bar, a quarter-inch Teflon dip tube, and a thermometer was fitted to an eight-inch Vigreax distillation column which in turn was fitted to a condenser and receiving flask. Under an atmosphere of dry nitrogen, the reaction flask was charged with $BiCl_3$ (1.6 g, 5.1 mmol) and n-decane (26 g) after which triethylaluminum (12.4 g, 109 mmol) was added dropwise while stirring. The temperature rose to 40° C. and a black precipitate formed. While stirring continuously, the mixture was heated to 120° C. and then gaseous methyl bromide (41.6 g, 438 mmol) was bubbled into the liquid phase through the dip tube over three hours. The black precipitate disappeared a few minutes after methyl bromide was first introduced. The reaction flask was cooled after all of the methyl bromide had been added. Distillate of 34 g, which collected in the receiving flask, was analyzed and found to contain 26 g ethylbromide and 8 g methyl bromide. The liquid in the reaction flask separated into two phases. The lower phase (2.2 g) was the catalyst. The upper phase was analyzed and contained 6.4 g trimethylaluminum and 0.90 g dimethylaluminum bromide; 83% of the upper phase was fractionally distilled to isolate 4.8 g trimethylaluminum (isolated yield=74%).

EXAMPLE 2

A reactor and distillation apparatus identical to that described in Example 1 was assembled. Under an atmosphere of dry nitrogen, the reaction flask was charged with $BiCl_3$ (1.6 g, 5.1 mmol) and n-decane (27 g) after which triethylaluminum (12.5 g, 109 mmol) was added over two minutes while stirring, whereupon a black precipitate formed. While stirring continuously, the mixture was heated to 120° C. and then, over the course of one hour, gaseous methyl bromide (42.1 g, 443 mmol) was bubbled into the liquid phase through the dip tube. The black precipitate disappeared a few minutes after methyl bromide was first introduced. The reaction flask was cooled after all of the methyl bromide had been added. The liquid in the reaction flask separated into two phases. The lower phase (3.0 g) was the catalyst. The upper phase was analyzed and contained triethylaluminum (2.8 g, 25 mmol), trimethylaluminum (4.5 g, 62 mmol) and dimethylaluminum bromide (0.63 g, 4.6 mmol).

EXAMPLE 3

A reactor and distillation apparatus identical to that described in Example 1 was assembled. Under an atmosphere of dry nitrogen, the reaction flask was charged with $BiCl_3$ (1.6 g, 5.1 mmol) and then triethylaluminum (12.3 g, 108 mmol) was added dropwise while stirring, whereupon a black precipitate formed. While stirring continuously, the mixture was heated to 120° C. and then, over the course of one hour, gaseous methyl bromide (40.7 g, 429 mmol) was bubbled into the liquid phase through the dip tube. The black precipitate disappeared a few minutes after methyl bromide was first introduced. The reaction flask was cooled after all of the methyl bromide had been added. The liquid in the reaction flask was analyzed and contained triethylaluminum (2.5 g, 22 mmol), trimethylaluminum (5.9 g, 82 mmol), and dimethylaluminum bromide (0.63 g, 4.6 mmol).

EXAMPLE 4

This example was conducted in a continuous manner without solvent and with distillation of both trimethylaluminum and ethyl bromide from the reaction flask. The reactor and distillation apparatus were similar to that used in Example 1 except for the following modifications: the reaction flask was fitted with a pressure-equalizing dropping funnel for adding triethylaluminum and the distillation head was fitted with an air-cooled condenser to condense trimethylaluminum and drain it to a collection flask maintained at about 50° C. to prevent alkyl bromide condensation. Non-condensed vapors then passed through the Vigreax column and into a second condenser where the alkyl bromides were condensed.

Under an atmosphere of dry nitrogen, the reaction flask was charged with triethylaluminum (12.0 g, 105 mmol) and then $BiCl_3$ (2.0 g, 6.3 mmol) was slowly added with stirring. Some "smoke" was observed, the temperature rose to about 55° C., and a black precipitate formed. The flask was heated to 120° C. and then slow feed of 116.8 g of methyl bromide vapor into the stirred liquid phase was commenced. Three minutes later, dropwise feed of 43.1 g (378 mmol) of triethylaluminum was commenced. After another ten minutes, the black precipitate had disappeared. After three hours, all of the triethylaluminum and methyl bromide had been added and the reactor was cooled. Total reactants were 55.1 g (483 mmol) of triethylaluminum and 116.8 g (1.23 mol) of methyl bromide.

The liquid in the reaction flask (51.6 g) separated into two phases. The lower phase (7.2 g) was the catalyst. The upper phase was analyzed and found to contain 22.4 g (197 mmol) of triethylaluminum, 13.6 g (189 mmol) of trimethylaluminum, 0.46 g (3.4 mmol) of dimethylaluminum bromide and other unidentified reaction products.

The liquid in the first receiving flask (7.9 g) was analyzed and found to contain 1.3 g (11.4 mmol) of triethylaluminum, 1.1 g (15 mmol) of trimethylaluminum, 0.077 g (0.56 mmol) of dimethylaluminum bromide, 2.9 g (27 mmol) of ethyl bromide, 0.42 g (3.0 mmol) of butyl bromide (from the butyl content of the triethylaluminum starting material) and other unidentified reaction products.

The liquid in the second receiving flask (73.0 g) was analyzed and found to contain 47 g (430 mmol) of ethylbromide, 26 g (277 mmol) of methyl bromide, and traces of triethylaluminum and trimethylaluminum.

The contents of the first receiving flask and the upper layer from the reaction flask were combined and 86% of the resulting mixture was fractionally distilled to isolate 11.1 g (154 mmol) of trimethylaluminum (isolated yield=71% based on triethylaluminum consumed).

EXAMPLE 5

This example is a continuous reaction similar to Example 4 except that a solvent was used.

Under an atmosphere of dry nitrogen, the reaction flask was charged with $BiCl_3$ (2.1 g, 6.6 mmol) and n-decane (27 g) after which triethylaluminum (12.6 g, 110 mmol) was added dropwise while stirring, whereupon the reaction temperature rose to about 40° C. and a black precipitate formed. The flask was heated to 120° C. and then slow feed of 132.5 g of methyl bromide vapor into the stirred liquid phase was commenced and the black precipitate began to disappear. Thirty seven minutes later, dropwise feed of 24.0 g (210 mmol) of triethylaluminum was commenced. After about three and one-half hours, all of the triethylaluminum and methyl bromide had been added and the reactor was cooled. Total reactants were 36.6 g (320 mmol) of triethylaluminum and 132.5 g (1.40 mol) of methyl bromide.

The liquid in the reaction flask (53.7 g) separated into two phases. The lower phase (3.6 g) was the catalyst. The upper phase was analyzed and found to contain 18.4 g (255 mmol) of trimethylaluminum, 0.64 g (4.7 mmol) of dimethylaluminum bromide and traces of other unidentified reaction products.

The liquid in the first receiving flask (20.6 g) was analyzed and found to contain 0.23 g (2.0 mmol) of triethylaluminum, 2.7 g (38 mmol) of trimethylaluminum, 0.13 g (0.95 mmol) of dimethylaluminum bromide, 14.8 g (136 mmol) of ethyl bromide, 2.2 g (16 mmol) of butyl bromide (from the butyl content of the triethylaluminum starting material) and traces of other unidentified reaction products.

The liquid in the second receiving flask (108 g) was analyzed and found to contain 65 g (594 mmol) of ethylbromide, 43 g (454 mmol) of methyl bromide, and traces of other unidentified reaction products.

We claim:

1. In a process for making trimethylaluminum by reacting a methyl halide with a trialkylaluminum compound having at least two carbon atoms in its alkyl groups under an inert atmosphere in the presence of a catalyst formed from a bismuth compound and recovering trimethylaluminum from the resultant reaction mixture, the improvement comprising adding said methyl halide to a reaction mixture at about atmospheric pressure containing said trialkylaluminum and said catalyst at a controlled rate such that said methyl halide reacts as it is added to form trimethylaluminum and an alkyl halide containing at least two carbon atoms while continuously distilling said alkyl halide and any unreacted methyl halide from the reaction zone thereby avoiding accumulation of either methyl halide or said alkyl halide in said reaction mixture and recovering trimethylaluminum from said reaction mixture.

2. A process of claim 1 wherein said trialkylaluminum is triethylaluminum.

3. A process of claim 1 wherein said bismuth compound is a bismuth halide.

4. A process of claim 3 wherein said trialkylaluminum compound is triethylaluminum.

5. A process of claim 4 wherein said bismuth halide is bismuth trichloride.

6. A process of claim 5 conducted at a reaction temperature of about 90°–125° C. in a liquid inert hydrocarbon solvent having a normal boiling point above the actual reaction temperature.

7. A process of claim 6 wherein said methyl halide is methyl chloride.

8. A process of claim 6 wherein said methyl halide is methyl bromide.

9. In a process for making trimethylaluminum comprising reacting a trialkylaluminum compound having at least two carbon atoms in its alkyl groups with a methyl halide under an inert atmosphere in the presence of a bismuth catalyst formed by reacting a trialkylaluminum compound with a bismuth compound wherein the improvement comprises:
   (A) continuously feeding to a reaction zone containing said bismuth catalyst at about atmospheric pressure (i) trialkylaluminum wherein the alkyl groups contain at least two carbon atoms and (ii) at least a stoichiometric amount, based on the formation of trimethylaluminum, of a methyl halide whereby said trialkylaluminum feed and said methyl halide react to form trimethylaluminum and an alkyl halide containing at least two carbon atoms and
   (B) continuously distilling said alkyl halide and any unreacted methyl halide from said reaction zone and
   (C) recovering said trimethylaluminum from said reaction mixture.

10. A process of claim 9 wherein said trialkylaluminum is triethylaluminum.

11. A process of claim 9 wherein said bismuth compound is a bismuth halide.

12. A process of claim 11 wherein said trialkylaluminum compound is triethylaluminum.

13. A process of claim 12 wherein said bismuth halide is bismuth trichloride.

14. In a process for making trimethylaluminum comprising reacting a trialkylaluminum compound having at least two carbon atoms in its alkyl groups with a methyl halide under an inert atmosphere in the presence of a bismuth catalyst formed by reacting a trialkylaluminum compound with a bismuth compound wherein the improvement comprises:

(A) continuously feeding to a reaction zone containing said bismuth catalyst (i) trialkylaluminum wherein the alkyl groups contain at least two carbon atoms and (ii) at least a stoichiometric amount, based on the formation of trimethylaluminum, of a methyl halide whereby said trialkylaluminum feed and said methyl halide react to form trimethylaluminum and an alkyl halide containing at least two carbon atoms and (B) continuously distilling said trimethylaluminum, said alkyl halide and any unreacted methyl halide from said reaction zone.

15. A continuous process of claim 14 wherein said trialkylaluminum is triethylaluminum.

16. A continuous process of claim 14 wherein said bismuth compound is a bismuth halide.

17. A continuous process of claim 16 wherein said trialkylaluminum is triethylaluminum.

18. A continuous process of claim 17 wherein said methyl halide is methyl bromide.

19. A continuous process of claim 18 wherein said bismuth halide is bismuth trichloride.

20. A continuous process of claim 17 conducted at a reaction temperature of about 100°–120° C. and at atmospheric or reduced pressure as required to cause trimethylaluminum to distill but not cause any substantial amount of triethylaluminum to distill from said reaction zone at reaction temperature.

* * * * *